US008758285B2

(12) United States Patent
Dallison et al.

(10) Patent No.: US 8,758,285 B2
(45) Date of Patent: Jun. 24, 2014

(54) SUPPORT DRESSING

(75) Inventors: Adam Dallison, Surrey (GB); Huw Pritchard, Nottingham (GB)

(73) Assignee: Flo Back Limited, London (GB)

( * ) Notice: Subject to any disclaimer, the term of this patent is extended or adjusted under 35 U.S.C. 154(b) by 191 days.

(21) Appl. No.: 12/681,971

(22) PCT Filed: Oct. 17, 2008

(86) PCT No.: PCT/GB2008/003546
§ 371 (c)(1),
(2), (4) Date: Apr. 7, 2010

(87) PCT Pub. No.: WO2009/050493
PCT Pub. Date: Apr. 23, 2009

(65) Prior Publication Data
US 2010/0210988 A1    Aug. 19, 2010

(30) Foreign Application Priority Data

Oct. 18, 2007    (GB) .................................... 0720373.0

(51) Int. Cl.
*A61F 13/06*    (2006.01)
(52) U.S. Cl.
USPC .......................................................... 602/61
(58) Field of Classification Search
USPC .................. 602/2, 60–62, 75, 41–43, 52–54, 602/57–58, 900, 12, 19; 128/877–879; 604/308; 606/204
See application file for complete search history.

(56) References Cited

U.S. PATENT DOCUMENTS

| | | | | |
|---|---|---|---|---|
| 3,068,860 A * | 12/1962 | Strazdas | .......................... | 602/19 |
| 4,860,736 A * | 8/1989 | Kaitz et al. | ..................... | 604/307 |
| 5,123,900 A * | 6/1992 | Wick | ................ | 602/41 |
| 5,275,284 A * | 1/1994 | Onotsky | ....................... | 206/441 |
| 5,706,800 A | 1/1998 | Cronk et al. | | |
| 5,709,651 A | 1/1998 | Ward | | |
| 6,318,362 B1 | 11/2001 | Johnson | | |
| 7,294,752 B1 * | 11/2007 | Propp | ............................. | 602/58 |
| 2004/0167456 A1 * | 8/2004 | Kingsford et al. | .............. | 602/48 |

FOREIGN PATENT DOCUMENTS

| | | | |
|---|---|---|---|
| FR | 2 697 156 A | 4/1994 | |
| FR | 2 838 957 A | 1/2003 | |
| FR | 2838957 A1 * | 10/2003 | ............. A61F 13/14 |
| FR | 2 867 969 A | 9/2005 | |
| WO | 96/01093 A | 1/1996 | |
| WO | 02/092141 A1 | 11/2002 | |
| WO | 2007/045931 A2 | 4/2007 | |
| WO | 2007/070946 A1 | 6/2007 | |
| WO | 2007/113597 A2 | 10/2007 | |

* cited by examiner

*Primary Examiner* — Patricia Bianco
*Assistant Examiner* — Raymond E Harris
(74) *Attorney, Agent, or Firm* — Brooks Kushman P.C.

(57) ABSTRACT

A support dressing comprises a conformable material that is capable of conforming to a body part when secured thereto; an adhesive for releasably securing the dressing to said body part; and at least one resilient component that has greater stiffness than the flexible material. It is particularly useful in preventing or reducing undesired torsion, especially of the lower back.

26 Claims, 3 Drawing Sheets

SUPPORT DRESSING

The present invention relates to supports. In particular, but not exclusively, it relates to supports for the back, especially for the lower back It is estimated that around 80% of the U.K. population will suffer from lower back pain during their lifetimes, costing UK businesses around £20 billion a year in lost productivity.

Activities such as sitting, lying, standing or moving with a poor posture, incorrect lifting techniques and various sports (e.g. squash, golf, rugby, football, gymnastics, etc.) can result in back injuries. These problems are often chronic, leading to long-term discomfort and pain.

Stress, obesity, a poor lifestyle and various medical disorders can also contribute to lower back pain. For example, patients with degenerative disorders such as arthritis and osteoporosis often have lower back problems.

The lower back is a dynamic structure, but is also able in healthy people to absorb impact and shock and to dissipate forces. It can provide great stability and flexibility and thereby allow significant freedom of movement. Indeed, this is usually taken for granted by healthy people. It can therefore come as a great shock when damage to the lower back results in severe changes to an individual's lifestyle. This can lead to a significant reduction in quality of life.

For the growing number of subjects who suffer from lower back problems there are a number of alternatives, but none are entirely satisfactory.

Many people simply live with pain or discomfort, or take pain killers.

Others may seek therapy and may consult various specialists. Surgeons are often consulted, although surgery is often a last resort and carries its own risks. Indeed many patients, especially elderly ones are reluctant to undergo such surgery because success rates can be low and there is always a risk of complications. For example, there has been recent adverse publicity in respect of hospital-acquired MRSA and *C. difficile* infections, illustrating the risks involved.

Other specialists such as physiotherapists, osteopaths or chiropractors are also often consulted.

They may use manipulation techniques to try to ease or reduce pain or discomfort. However such techniques do not work for everyone. Indeed, it is advisable not to use such techniques at all for certain patients, e.g. for patients with severe osteoporosis.

Various alternative therapies also exist and have gained increasing popularity over recent years. These range from well known alternative therapies such as acupuncture, hydrotherapy, etc. to more unusual "new age" or spiritual therapies. However, the effectiveness of many such therapies is highly questionable. Furthermore there are many unscrupulous practitioners involved in alternative therapy. Therefore many people seek to avoid the risks involved in alternative therapy.

It is therefore generally preferred to take more established approaches.

One such approach is to use a support, which may be in the form of a dressing or a belt for example.

Dressings in the form of heat plasters can be purchased. These incorporate a substance, often in a pouch, which releases heat over a period of time when activated (e.g. by opening and the resultant exposure to air). The release of heat can increase the comfort of certain patients in the short term, but often does very little for altering mechanical dysfunction or for reducing inflammation.

Cold packs are therefore sometimes used as an alternative. Indeed they are often preferred to heat packs. They are often used to treat or prevent sporting injuries. However they tend to be most effective if applied very soon after an injury or a sporting activity has occurred. They can be uncomfortable to wear and this can result in poor patient compliance. Indeed in some cases they may cause injuries to the skin. An additional important point is that it is necessary to prepare and store cold packs in advance.

An alternative is to use lumbar belts. These are worn around the back. However patients often find these thick, heavy and cumbersome to wear. Furthermore, extensive research has shown that they are often of little benefit in treating or preventing lower back injury.

A simple alternative is to use strapping tape. Indeed such tape is often used by professional physiotherapists or practitioners of sports medicine. It is inexpensive and there are very few contraindications for use. It has also been shown to aid proprioception, increase stability, prevent aggravation of injury, and speed up healing time; whilst still allowing a degree of mobility.

Unfortunately, however, taping of the lower back can be very time consuming and requires skill an experience to be done properly. Tape is generally cut from two types of roll and applied in a four step process. This technique can greatly assist in limiting undesired flexion (forward bending). However, injury and pain are not incurred simply by movement in this direction. It has long been established that rotation (torsion) of the spine is a significant contributory factor to lumbar disc injury.

Indeed, excessive torsion may damage fibers of the annulus fibrosis, the ilio-lumbar ligament (or other ligaments) spinal muscles, the joint capsule, vertebrae, spinal nerves, etc. However traditional tapes are very flexible and do not have a major degree of resistance to torsion.

As an alternative to extensive taping, various support dressings have been proposed. These can provide greater convenience than taping techniques, especially with respect to ease of application. However, they are not necessarily any more effective.

For example, in international patent application number PCT/AU2006/001938 a support for the lower back is described that is said to be in the form of four sides of a square. It is claimed that this "reduces flexure of the lumbar spine and maintains the wearer's neutral spine alignment". However the support for the lower back described in PCT/AU2006/001938 includes no special features to reduce the risk of injuries or pain that may be incurred due to excessive or undesired torsion. It therefore appears to be no more effective than the traditional taping technique in this regard.

FR 2838957 also discloses a dressing for the lower back. This is said to aid posture support. It can even incorporate an audible alarm to warn a wearer of the dressing at a stage when a risky posture is adopted. A figure is provided in FR 2838957 showing a poor posture being adopted. Here a user is shown bending to pick up a weight without bending his legs. Again, however, this concentrates upon injuries/damage due to flexion and there is no consideration of the technical problem of pain or injuries being caused /aggravated through torsion. Furthermore, the dressing disclosed in FR 2838957 has no special features to deal with this problem.

U.S. Pat. No. 3,068,860 describes a back plaster that exerts pressure on the spinal column to provide relief from backache. However, exerting pressure on the back of the user may cause further problems as the architecture of the back adjusts or reacts to the additional pressure. Additionally, the device of U.S. Pat. No. 3,068,860 aims to compress lower lumbar segments, which although may seek to prevent unwanted movement may also, as discussed above, cause additional problems in itself by forcing the back into rigid positions. Furthermore, a certain degree of spinal mobility should be permitted to allow fluid dynamics to exchange around the annular disc.

There is therefore a major need for an improved dressing that prevents or reduces the risk of injuries (especially injuries that are caused through undesired or excessive torsion) or at least to alleviate one or more adverse effects of such injuries once they have occurred.

This is a major and long-standing need, as can be attested by many physiotherapists worldwide. However to date there has still been no satisfactory solution.

The present inventor has now come up with a surprisingly elegant solution to this problem.

According to the present invention there is provided a support dressing that comprises:
a) a conformable material that is capable of conforming to a body part when secured thereto;
b) an adhesive for releasably securing the dressing to said body part; and
c) at least one resilient component that has greater stiffness than the flexible material.

The at least one resilient component can serve to prevent or reduce undesired torsion of said body part.

It is not however limited to this purpose. It can for example additionally, or alternatively, be used to prevent or reduce undesired bending of said body part.

The resilient component can be formed of any material that provides the desired resilience; whilst still having at least some flexibility to take into account normal body movements.

Such materials include for example plastics, metals or metal alloys, card, wood, composite materials, laminates, carbon fibre, etc.

Less preferably, they include bone or ivory (which are sometimes used to provide supports in corsetry).

The resilience of the material is preferably such, so that when it has been bent/twisted it seeks to move back towards/close to its previous position. This is due to the additional resistance against undesired movement being sensed by proprioreceptors in the skin.

The material therefore preferably has a "memory" whereby it seeks to return/recoil at least to some degree towards its previous orientation.

A wearer of the dressing will therefore normally need to exert additional force when bending/twisting a body part to which the dressing has been applied, relative to a situation where the resiliently deformable material was absent.

This can make bending or twisting a much more conscious movement than it would otherwise be. Whilst a wearer of the dressing can usually overcome the resilience the material by exerting additional force, the presence of the material makes it more likely that the user will not bend/twist, at least to the same degree. This can be very important in preventing or treating injuries. Furthermore, the dressing is non-elastic, although flexible, to assist in preventing undesired twisting or bending movement.

Desirably, the dressing has a plurality of arms. More desirably, it has at least three arms or at least four arms. Preferably two or more (or even all) of the arms are non-parallel Most desirably, the dressing has four arms and is generally cruciate in shape. It is not however essential that all arms be of the same length, as discussed later in connection with the drawings.

The at least one resilient component may also have a plurality of arms and may also be generally cruciate in shape. If desired it can be formed by overlapping elongate members. These may then be held in the desired position simply by the other parts of the dressing (e.g. if the dressing is a laminate structure). Alternatively they may be physically joined together (eh by soldering, glue, heating, riveting, stapling etc). In a preferred alternative, a unitary structure is provided in the desired shape (e.g. by cutting a material to shape from a blank, by stamping it out, by forming it in a mould, by casting, etc.). Thus the at least one resilient component is preferably a unitary component. This can provide increased strength and can simplify manufacture It is preferred that the at least one resilient component is generally the same shape or a similar shape as the shape defined by the periphery of the dressing. It may also be to the same scale. However in most instances it is preferred that it represents a generally scaled down version of said shape. This allows the conformable material to extend beyond/overlap the resilient material so that it can attach to other regions (e.g. to a lower layer of material or even directly to the skin).

The at least one resilient component may be located within the dressing and this is generally preferred. For example it may be located between outer and inner layers of conformable material. It may be secured in place by adhesive, by laminate or by mechanical means (e.g. internal pockets, hoops, stitching or restraints). Indeed it may simply be held in place by virtue of being between two or more layers that are attached to one another.

Alternatively, and less preferably, the at least one resilient component may be at least partially exposed on the outside of the dressing. For example one or more struts may be secured to an outer layer of fabric. (This is analogous to exposed resilient struts of a kite, which can resist excessive movement or torsion, but can flex to a certain degree.)

The dressing can be used for any desired purpose.

Preferably however it is used to treat or prevent pain, injury or discomfort.

More preferably, the dressing is used as a support dressing for the back.

Most preferably, the dressing is for the lower back. The lower back is particularly prone to injury through torsion and therefore the invention is particularly useful here. Muscles, ligaments, nerves and joint capsules in this region (e.g. the annulus fibrosis, the ilio-lumbar ligament and various spinal muscles) can be particularly susceptible to damage arising due to undesired/excessive torsion.

A dressing of the present invention is particularly useful in preventing or treating such damage (including reducing pain or discomfort that might occur in the absence of said dressing).

The dressing is of course not limited to being used as a dressing for the back. It can be used in any desired location. Indeed it can be used on any part of the body where a degree of protection against an undesired movement (especially undesired torsion) is desired. For example, it may be used on the neck, shoulder, arm, leg or on a part thereof (e.g. ankle, wrist or knee).

Preferably, however, the dressing is not used or shaped for use on the nose. It is therefore very different from the type of dressing disclosed in U.S. Pat. No. 6,318,362 for example. This dressing is used simply to enlarge the nasal passages and not to prevent or ameliorate injury due to excessive/undesired movement. On the contrary it is used to move a body part (the nose) out of its normal position so as to enlarge nasal passages and to allow greater throughput of air. The invention disclosed in U.S. Pat. No. 6,318,362 therefore goes in a completely different direction from the present invention. It provides no anti-torsional effect and simply uses parallel strips of material to force open the nasal cavity.

The dimensions of a dressing of the present invention can of course vary with the application for the dressing and are therefore not limiting.

In the case of a dressing for the lower back, for example, it is preferred that the dressing is relatively large so as to allow the base of the dressing to contact the upper buttock region (sometimes known as the region of the sacrum) and to allow the upper parts of the dressing to contact the lumbar region at both sides of the spinal column. Dressings in this position are illustrated for example in FIG. 3 of FR 2838957, for example, although they do not of course incorporate the at least one resilient component used in the dressing of the present invention.

Typically such a dressing will be at least 10 cm long measured from the base to the uppermost tip (along the maximum dimension). Preferably it will be at least 15 cm long. Desirably it will be at least 5 cm or at least 10 cm wide when measured across its maximum width. Clearly such dimensions are very different from those found in the nasal dressings discussed above.

The dressing of the present invention may optionally incorporate various additional features.

For example, it may include a material that can be used to heat up or cool down the body part to which it is applied. Thus for example a heat pack or a cooling pack (such as an ice pack) may be incorporated. Preferably, the dressing is non-elastic.

If desired, the dressing may be provided with one or more apertures for improving moisture vapour permeability and/or for reducing adhesion. Such apertures may extend entirely through the dressing. The apertures may be defined by any desired shape, but are preferably defined by a rounded (e.g. circular) shape. They can be provided at any desired location. For example one or more apertures may be provided within each arm of a multi-armed dressing.

For example if the dressing has a plurality of arms each arm may be provided with a clearly visible aperture. Any desired shape of aperture may be provided. For example each arm may be provided with a circular aperture. Indeed the arms may terminate with annular structures of the type illustrated in FR 2838957, for example.

The apertures can be cut out of a pre-existing dressing with a sharp instrument (e.g. scissors or a scalpel). Alternatively, the dressing may be provided with such apertures already present.

The size of the apertures can vary. However where an aperture is present it is desired that it leaves an area of at least 1 cm$^2$ or at least 2 cm$^2$ of exposed skin. More preferably the area is at least 5 cm$^2$. The presence of large areas of exposed skin can be useful in aiding removal of the dressing especially if it is present at an area where here is a large amount of body hair. It may also be advantageous in allowing sweat to evaporate, especially if the dressing comprises material with low moisture vapour permeability.

In many instances the dressing will be provided with both an outer layer of conformable material and an inner layer, as discussed earlier. The two layers may be formed of the same material. More preferably however they are formed of different materials.

The outer layer can provide a protective function. It may for example be formed from a polyurethane, such as those described for use as a backing layer in U.S. Pat. No. 5,709,651, for example.

It may conveniently be formed from a material traditionally used by physiotherapists for taping and strapping. For example traditional zinc oxide taping material can be used and is advantageous in that it carries its own adhesive. This adhesive can be used for attaching the conformable outer layer to the inner layer of cushioning material. The resilient material will generally be located between these two layers and the adhesive can therefore be sufficient to hold it in place at a desired position.

The inner layer is preferably highly porous. If desired, it may provide a degree of cushioning and/or absorbency. Any appropriate material can be used. Preferred materials include non-woven materials (although woven materials can be used of desired). One such material that is commonly used in dressings is sold under the trade mark of Hypafix.™ and is available from Smith & Nephew p.l.c. This includes not only a non-woven layer but also an adhesive and a release paper. Thus it can be conveniently be used to provide an adhesive for attaching the dressing to a patient. The release paper allows the adhesive to be exposed only when desired. Thus the dressing may be in the form of a "sandwich structure" in which the resilient material is located between an upper protective layer and a lower layer of cushioning material.

Indeed a dressing may be made in situ by forming such a sandwich and, if necessary, cutting it to shape. Kits can even be provided for such a purpose, as discussed later. Here adhesive will normally be used to join the layers together, although there are many other possibilities including stitching, lamination etc, as discussed earlier.

The conformable material of the support dressing may comprise a silicone material, such as that described in WO2007/113597, or a material such as those described in WO2007/045931. Alternatively, the suitable conformable material may be any woven or non-woven, natural or synthetic material. Preferably, the dressing comprises a polyurethane material (PU). Preferably, the material is breathable and waterproof.

The adhesive method of the present invention may be described as in WO 02092141. The adhesive is most preferably a non-allergenic and/or medical grade adhesive.

It will be appreciated from the foregoing description that the present invention has major applications in treatment, including prophylaxis.

It can for example be used to reduce pains, strains, aches, mechanical dysfunction (e.g. hypermobility or hypomobility), etc., or to reduce the risk thereof.

It therefore has particular benefits in physiotherapy or orthopaedic medicine.

It can be applied easily and quickly. Preferably the resilient material has sufficient rigidity to prevent the dressing flopping over on itself when it is held. Thus it can preferably be held in an upright position in one hand and can be smoothed/placed onto a patient using the other hand.

It can also be used for sports. Indeed it is particularly useful in sports where the lower back of the body is prone to twist in a potentially dangerous or painful manner.

Such sports include golf, racket sports, gymnastics, cricket, baseball, athletics (e.g. discus throwing, hammer throwing, pole vaulting), diving and many contact sports (e.g. wrestling, rugby, football, American football), etc.

The dressing of the present invention can also be used to improve posture. This can be useful generally for health/educational purposes. It may also be useful more specifically, e.g. for models, actors, sports people, etc. Indeed the dressing may be used as a guide or aid for correct posture. It can therefore be worn by healthy people.

If desired, advanced versions of a dressing of the present invention may even incorporate one or more sensors or alarms, although in most case these will be absent in order to minimise costs and complexity.

For example an alarm may emit a signal if a dangerous posture is adopted/likely to be adopted (e.g. a posture involving an undesired degree of torsion). Such alarms are described in FR 2838597, for example. Sensors may be provided at various places to allow posture to be analysed via a computer. This can be particularly useful in illustrating to a person wearing the dressing when an incorrect posture has been adopted. Alarms and/or sensors may be operatively linked to the at least one resiliently deformable component.

The invention can even be used generally in the workplace. It is particularly suitable for manual jobs where there is a risk of injury to the back or other body parts, especially via undesired torsion. Such jobs include jobs in farming, construction, renovation, house moving, nursing (where it is often necessary to move/lift patients), etc.

However they can also include non-manual jobs where a person may twist to access various pieces of equipment (e.g. computer consoles, telephones, printers, etc). Indeed office workers frequently complain of back problems.

It will therefore be appreciated that the dressing of the present invention has an extremely large number of applications.

It is the combination of the rigid support and conformable material that provides the advantage of the present invention over known taping methods and lumbar belts. The internal rigid component limits torsional and combined motion forces, which are clinically known to be the cause of many back injuries. However, the torsional rigidity is not of the extent that it is a discomfort to the user and does not inhibit day to day activity, provided that the correct posture is maintained. Maintaining the correct posture is aided by the support of the invention Supports that do not contain a rigid component do not provide the necessary support to treat or prevent injury through the maintenance of a correct posture. However, supports that consist entirely of a stiff rigid component have the disadvantage that they do not conform to the users body and thus movement may cause detachment of the support from the user, and such supports are generally uncomfortable to wear.

The supports of the present invention provide the stabilising rigid component in combination with a conformable material to ensure continuous adhesion and comfort, whilst still providing support and preventing or treating injury.

The support of the present invention also provides the advantage that it can be applied by the user to the user's own back, i.e. no intervention or assistance from a medical professional or a third party is required. The rigid strut is preferably pre located and sealed by the layers of the conformable material which reduces the likelihood of mis-placement by the user.

The material of the conformable component is preferably breathable and waterproof. This provides additional comfort to the user and also prevents detachment of the support due to perspiration, bathing, showering or swimming.

In addition to the dressing per se, the invention also includes various kits.

For example it includes a kit for making a dressing of the present invention comprising the conformable material and at least one resilient component described earlier.

The kit optionally also comprises one or more of the following:
a) instructions for use in making the dressing
b) adhesive
c) an additional conformable material
d) cutting means
e) release paper.

The cutting means (e.g. scissors or a cutting blade, such as a scalpel) may of course be dispensed with if the components are already cut to shape.

Furthermore, adhesive will not be needed if the conformable material and/or the cushioning material do not already carry adhesive.

If adhesive, is supplied it is preferably a pressure sensitive adhesive. Such adhesives are described in U.S. Pat. No. 5,709, 651 for example and include acrylic adhesives, and silicone adhesives. Medical grade adhesives are most preferable. Of course, non-allergenic adhesives are most preferable.

The cushioning material may also be dispensed with if the dressing is comfortable enough for a patient to wear without additional cushioning.

Instructions for use are of course only needed if a person making the dressing does not already know to make it. Thus such instructions are also optional. If instructions are provided they can be in any desired form, e.g. as drawings, symbols or in writing.

In most cases however it is envisaged that the dressing will be purchased in a form in which it is already complete. Normally it will be provided in a sealed package. It may be in sterile form. For example it may have been subjected to UV irradiation and/or ethylene oxide prior to packaging.

The dressing may of course be sold in a kit together with one or more additional dressings (which may be the same or different as a dressing of the present invention). For example it may be included in a first aid kit, a sports kits or a general medical kit.

The kit may optionally include instructions for use in applying the dressing.

Having described the present invention in general terms, it will now be described by way of the following non-limiting example, with reference to the accompanying drawings; wherein.

Figure 1:
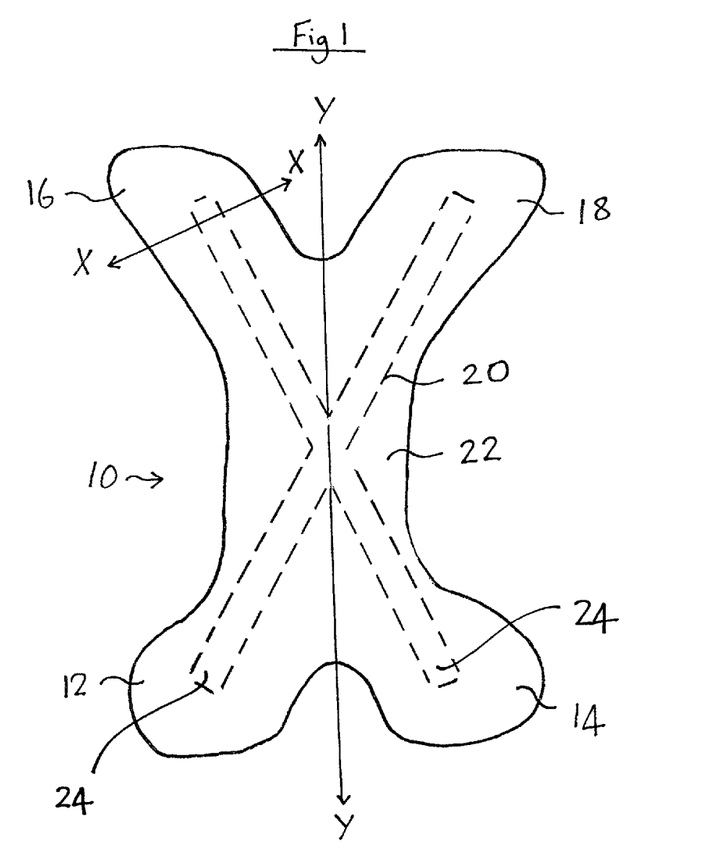
FIG. 1 shows a view from above of a dressing for a lower back.

Turning now to FIG. 1, a dressing for the lower back 10 is shown. It can be seen that the dressing 10 is generally cruciate in shape and therefore has four arms. Two relatively short arms 12, 14 and two relatively long arms 16, 18 are provided.

The two relatively long arms 16, 18 are designed to contact the upper buttock region of a patient wearing the dressing, where there are relatively few proprioceptors and a higher contact area is desired.

The two relatively short arms 12, 14 are designed to contact a higher region on the back on either side of the spine. Here the concentration of proprioceptors is higher (for a given area) and therefore the contact area need not be as great.

Thus the dressing shown is not symmetrical about a horizontal axis (when in use). It is however bilaterally symmetrical about a vertical axis, which is shown as Y-Y in this Figure.

Figure 2:
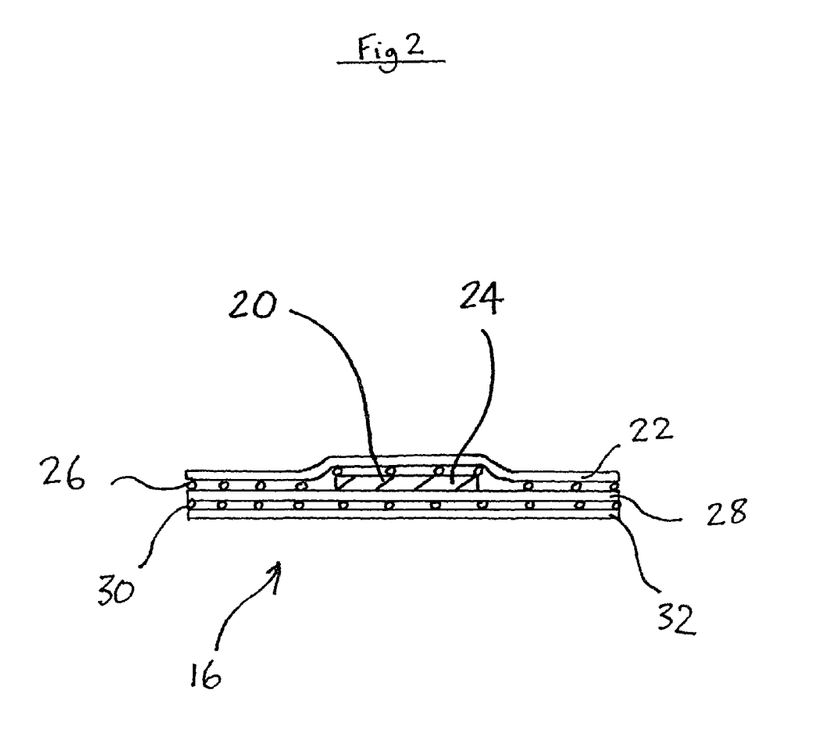
FIG. 2 shows a cross section through the part of FIG. 1 indicated by the line X-X.

Turning now to FIG. 2, this shows a cross-section taken through an arm 16 of the dressing 10 and along the line X-X shown in FIG. 1. For ease of reference the cross section is shown schematically in FIG. 2 and is not to scale.

It can be seen from this cross section that the dressing comprises a plurality of components.

An upper layer 22 is formed of a protective backing fabric. This fabric is conformable so as to conform to the contours of the skin. It also carries an adhesive 26.

For illustrative purposes the adhesive 26 is shown as discrete blobs or spots. This is because it does not form a continuous layer, but is discontinuous. This allows moisture vapour permeability and therefore assists in allowing sweat to evaporate through the dressing. It also assists in aiding subsequent removal of the dressing, by reducing the quantity of adhesive and the surface area of a patient in contact with adhesive.

It can be seen from FIG. 2 that the upper layer 24 is attached via the adhesive 26 to a central relatively rigid strut 24 of resilient material and is also to a conformable lower layer of non-woven material 28.

The non-woven material 28 carries its own adhesive 30, which attaches it to a release paper 32. If desired, at least part of the release paper 32 may extend out from the remainder of the dressing 10 so it can be easily gripped and removed prior to application of the dressing (not shown). Alternatively, overlapping release papers may be provided. One of the release papers can then be gripped in the region of the overlap to facilitate removal.

Turning back to FIG. 1, it can be seen that there are actually two rigid struts 24 which overlap at a central position to form an internal cruciate structure 20 located within the boundaries of the cruciate dressing 10. This internal cruciate structure 20 provides the dressing 10 as a whole with increased rigidity.

Thus, for example the dressing 10 can advantageously be held at a single position between thumb and forefinger whilst it is being applied to the skin without it flopping over. (This facilitates applying the dressing to a patient and reduces potential wastage. It contrasts with many prior art dressings that have no real internal structural supports and can simply flop down under their own weight and adhere to themselves and are thus rendered unusable.)

More importantly the overlapping struts 24 provide a much greater resistance to torsion than would occur if they were absent. The struts 24 can flex or twist to some degree, but, as they so, their resilience urges them to seek to return to their previous orientation/close thereto. This in turn causes an opposing force to be exerted on the skin of a person to whom the dressing has applied, which acts as a stimulus.

This stimulus is sensed by the person via proprioreceptors in the skin and will normally cause the person not to twist further in a given direction, especially if the person has previously been warned of the risks of such action. Indeed, if the person continues to twist then a greater reactive force will be exerted by the struts 24 and the stimulus will be greater, causing additional stimulation of proprioreceptors in the skin and a further indication to the person wearing the dressing that the torsional movement is potentially dangerous.

It is important to bear in mind that the struts 24 do not have to be particularly strong. Their main function is to exert a stimulus and not to physically prevent torsion. Indeed if a patient chooses to twist in an undesirable manner then the patient will normally be free to do so. However the patient will then be fully aware of this via the stimulus transmitted via the skin's proprioreceptors and will therefore have had ample opportunity to have taken preventative action, if desired.

However, in most cases it is envisaged that patient compliance will be very high, given the stimulus provided by the dressing against possibly dangerous movement. Thus the dressing 10 can aid significantly in reducing pain or discomfort or the risk thereof.

The dressing 10 is of course also useful in preventing or reducing the risk of injury.

It may even simply act as an aid for correct posture, as discussed earlier herein.

It should also be noted that the dressing 10 is of course not limited to the particular shape shown in FIG. 1. Any shape or structure can be provided as long as the dressing fulfils its function Various non-limiting alternative shapes for support dressings are shown in FIG. 3, with the resilient support indicated by dotted lines.

Figure 3:
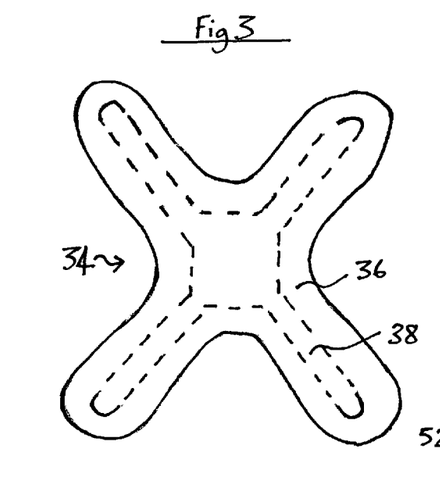
FIGS. 3 to 6 provide views from above of various alternative shapes for dressings of the present invention. (Many more shapes are of course possible.)

FIG. 3 shows a cruciate support dressing 34 comprising a conformable material 36 and a resilient support structure 38 in which the arms are of equal size.

Figures 4, 6:
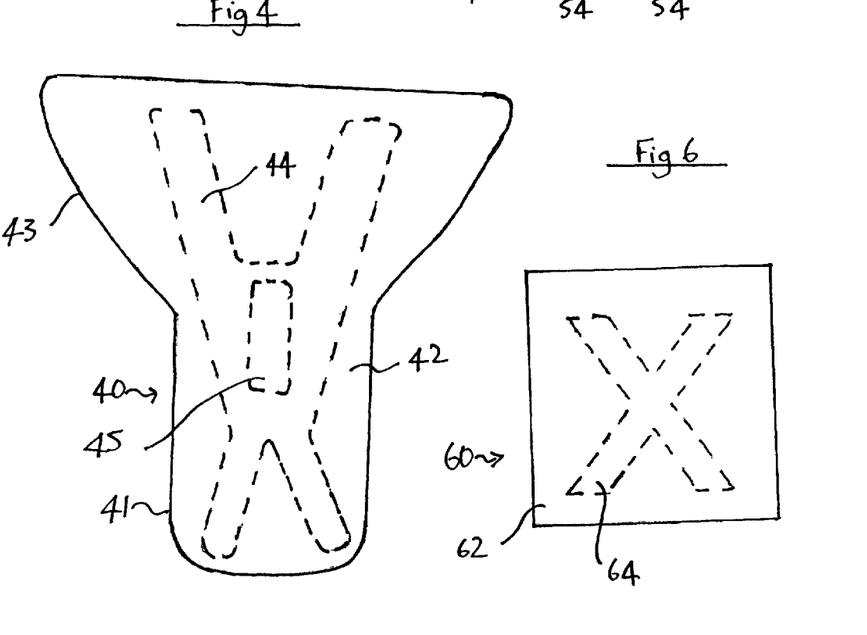

FIG. 4 shows a support dressing 40 in which one end 43 is much wider than the other end 41. The wider end 43 is for contacting a region where the number of proprioreceptors for a given area of skin is relatively low. The less wide end 41 can be used for contacting a region where the number of proprioreceptors is relatively high. A generally cruciate resilient support structure 44 is also shown, which has a central aperture 45.

Figure 5:
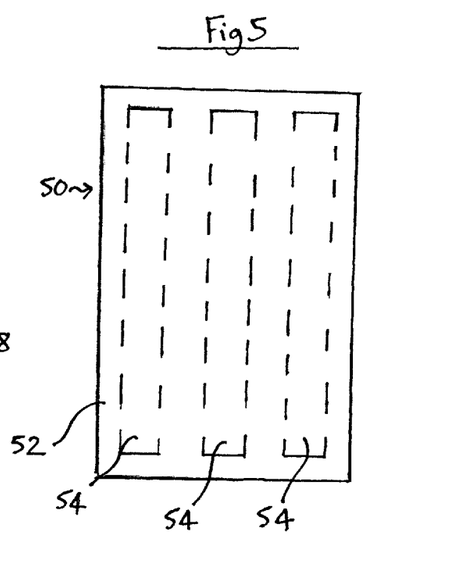

FIG. 5 shows a generally rectangular support dressing 50 comprising a plurality of parallel resilient members 54 and a conformable material 52 that covers the resilient members 54.

FIG. 6 shows a generally square support dressing 60 comprising a cruciate support structure 64 and a conformable material 62 that covers the resilient support structure 64.

[NB: In FIGS. 1, and 3 to 6 the dotted lines illustrate a resilient structure located below an outer cover layer of material. The resilient structures are therefore not directly visible when the support dressings are in use. However, in practice, contours defining the general periphery of the resilient structures will normally be identifiable because the height of the dressing will normally be greater in the region of the resilient material than in the region where resilient material is not present.]

EXAMPLE

Patients (n=38) with back pain were given an example of a support of the present invention (A) and a known support (B) (as described in PCT/AU2006/001938). Support (B) provides for either a lumber (lower back) plaster comprising an open square shaped support or a thoracic (upper back) plaster comprising an X shaped support. 17 subjects compared (A) to the lumber support (B) and 21 subjects compared (A) to the thoracic support (B). The patients were asked to compare each support in terms of general back support, maintenance of lumbar spine position, posture maintenance, rigidity, ability to prevent twisting movement, ability to prevent sideways bending and ability to limit combined movement of forward bending and twisting.

Patients were not told in advance of the trial the object or purpose of each support plaster. The results are shown below.

| All numbers in % | | | |
|---|---|---|---|
| | Thoracic group | Lumbar Group | Combined |
| 1. What device provides the greater back support? | | | |
| B | 23.8 | 5.9 | 14.8 |
| A | 71.4 | 94.1 | 82.8 |
| Equal | 4.8 | | 2.4 |
| 2. Which device is better at maintaining your lumbar (low back) spine position? | | | |
| B | 19 | 11.8 | 15.4 |
| A | 81 | 88.2 | 84.6 |
| Equal | | | |
| 3. Which device maintains your general spine in a better posture? | | | |
| B | 14 | 0 | 7 |
| A | 72 | 100 | 86 |
| Equal | 14 | | 7 |

-continued

All numbers in %

| | Thoracic group | Lumbar Group | Combined |
|---|---|---|---|
| 4. Which support is more rigid? | | | |
| White | 23.8 | 5.9 | 14.8 |
| B | 76.2 | 94.1 | 85.2 |
| A | | | |
| 5. Which device is better at reducing twisting/rotation movements? | | | |
| B | 14 | 11.8 | 12.9 |
| A | 72 | 76.4 | 74.2 |
| Equal | 14 | 11.8 | 12.9 |
| 6. Which device is better at preventing bending to the side? | | | |
| B | 14 | 11.8 | 12.9 |
| A | 72 | 82.3 | 77.2 |
| Equal | 14 | 5.9 | 9.9 |
| 7. Which device is better at limiting a combined movement of forward bending and twisting? | | | |
| B | 19 | 5.9 | 12.4 |
| A | 76.2 | 94.1 | 85.2 |
| Equal | 4.8 | | 2.4 |

B = Support of PCT/AU2006/001938
A = Example of a support of the present application These results clearly show that the support of the invention provides greater stability, rigidity and support to both upper and lower back simultaneously than those already known. The inclusion of the internal strut, which is not present in either the thoracic or lumbar device (B), provides the support needed to limit twisting and sideways bending movement. This is critically important, for it is clinical known that most disc injuries occur under this direction of movement when combined with flexion (forward bending).

It should also be noted that the subjects found the support of present invention (A) comfortable to wear.

GLOSSARY

Various terms used herein will now be described in greater detail.

"Support"

This term is used broadly to include anything that prevents or reduces the likelihood of a part of the body moving in an undesired manner. Thus it includes dressings that may prevent undesired flexing or torsion.

"Dressing"

This term is not limited to dressings for wounds or injuries, but also includes dressings that be used as a support (see above). Thus, for example sports dressings or orthopaedic dressings are included. A dressing will normally comprise a flexible fabric and an adhesive. It may be provided in a sealed package and will often be in sterile form within said package.

"Treatment"

This term includes not only the treatment of pre-existing conditions, but also preventative (prophylactic) treatments. Prophylactic treatments can be particularly important for people prone to or at risk of injury, e.g. the elderly, players of certain sports (e.g. golf, contact sports, racket sports, etc.) and for people in professions involving a potential risk of injury to parts of the body (especially due to excessive torsional movement).

The term "treatment" includes treatment of any undesirable effects/symptoms of a condition, including injuries, aches, pains, strains, discomfort, dysfunctions, etc.

Thus it is not essential that a treatment provide a complete cure, as long as there is some benefit to the patient. In the case of the present invention treatment will normally be incurred simply by applying the dressing at an appropriate location and leaving it on a patient for sufficient time for it to have a desired effect.

"Arm"

This term is used to describe a part of the dressing that extends from another part and has a distinctive shape. Several arms may be present. For example if the dressing has a cruciate shape four arms may extend from a central region. The arms may be elongate, but this is not essential. The arms may even be of different sizes and/or different shapes.

"Release paper"

This includes any material that can be easily peeled away from an adhesive dressing so as to expose the adhesive for use. It is not limited to paper, but includes a wide range of flexible materials, as is well known in the art. Silicone release papers are preferred, but are not of course essential.

"Torsion"

This includes rotation or pivoting about any axis. Undesired torsion is such movement that causes or is likely to cause injury, strain, pain, discomfort or mechanical dysfunction.

The invention claimed is:

1. A support dressing for preventing or reducing torsion of a body part, the support dressing comprising:
  a) a conformable material that is capable of conforming to a body part when secured thereto;
  b) an adhesive for releasably securing the dressing to said body part; and
  c) a unitary resilient component that has greater stiffness than the conformable material, wherein the dressing is cruciate in shape and the unitary resilient component is generally cruciate in shape and is configured to prevent or reduce undesired torsion of said body part.

2. A dressing according to claim 1; wherein the resilient component has a first pair of two arms and a second pair of two arms, the first pair of arms being longer than the second pair of arms.

3. A dressing according to claim 2; wherein the first pair of arms are configured to contact an area of said body part having a relatively low concentration of proprioreceptors and the second pair of arms are configured to contact an area of said body part having a relatively high concentration of proprioreceptors.

4. A dressing according to claim 3; wherein the first pair of arms have a higher contact area than the second pair of arms.

5. A dressing according to claim 2; wherein the first pair of arms is configured to contact a lower lumbar region of a patient and the second pair of arms is configured to contact an upper lumbar region of a patient.

6. A dressing according to claim 1 that is at least 10 cm long when measured across its maximum length.

7. A dressing according to claim 6 that is at least 15 cm long when measured across its maximum length.

8. A dressing according to claim 1 wherein the at least one resilient component can prevent or reduce undesired bending of said body part.

9. A dressing according to claim 1; wherein the at least one resilient component comprises or consists of one or more of the following materials: a plastics material; a metal or alloy; card, wood, a composite material, a laminate.

10. A dressing according to claim 1 that is a dressing for the back.

11. A dressing according to claim 1 that is a dressing for the lower back.

12. A dressing according to claim 1 that is at least 10 cm wide when measured across its maximum width.

13. A dressing according to claim 1 incorporating material that serves to heat up or cool down said body part.

14. A dressing according to claim 1 comprising one or more apertures that extend though the dressing so as to improve moisture vapour permeability and /or to reduce adhesion.

15. A dressing according to claim 1 that comprises an outer layer of conformable material and an inner layer of conformable material, with the at least one resilient component being located between said outer and inner layers.

16. A dressing according to claim 1 that further comprises one or more sensors or alarms.

17. A dressing according to claim 1; for use in medicine.

18. A dressing according to claim 1; for use in treating, preventing or reducing one or more of:
   a) injury
   b) strain
   c) aches
   d) pain
   e) discomfort
   f) mechanical dysfunction.

19. A dressing according to claim 1; for use in improving posture.

20. A dressing according to claim 1; for use in sport.

21. A dressing according to claim 1; for use in the workplace.

22. A dressing according to claim 1; for use in treating or preventing injury to the lower back.

23. A dressing according to claim 1; for use in treating or preventing injury to one or more of the following: vertebrae, nerves, ligaments, muscles, ligaments or joint capsules.

24. A kit comprising a dressing according to claim 1 and one or more of the following:
   a) instructions for use in applying the dressing
   b) one or more other dressings
   c) a sealed container.

25. A kit for making a dressing according to claim 1;
   wherein the kit comprises said conformable material and said at least one resilient component;
   said kit optionally comprising one or more of the following:
   a) instructions for use in making the dressing
   b) adhesive
   c) a further conformable material
   d) cutting means
   e) a release paper.

26. A support dressing for preventing or reducing torsion of a body part, the support dressing comprising:
   a) a conformable material that is cruciate in shape and configured to conform to a body part when secured thereto;
   b) an adhesive for releasably securing the dressing to said body part; and
   c) a unitary resilient component that is generally cruciate in shape, has greater stiffness than the conformable material, and is configured to prevent or reduce undesired torsion of said body part;
   wherein the unitary resilient component includes a first pair of two arms and a second pair of two arms and the first pair of arms are configured to have a higher contact area with the body part than the second pair of arms.

* * * * *